(12) United States Patent
Burdett et al.

(10) Patent No.: US 8,232,813 B2
(45) Date of Patent: Jul. 31, 2012

(54) SENSOR CIRCUITS

(75) Inventors: Alison Burdett, Abingdon (GB); Paul Padden, Abingdon (GB); David Townsend, Swindon (GB); Sharon Louise Thornton, legal representative, Swindon (GB); Christopher David Townsend, legal representative, Swindon (GB); Richard Andrew Martin, legal representative, Swindon (GB)

(73) Assignee: Toumaz Technology Limited, Oxfordshire (GB)

( * ) Notice: Subject to any disclaimer, the term of this patent is extended or adjusted under 35 U.S.C. 154(b) by 817 days.

(21) Appl. No.: 12/097,871

(22) PCT Filed: Oct. 3, 2006

(86) PCT No.: PCT/GB2006/050311
§ 371 (c)(1),
(2), (4) Date: Sep. 9, 2008

(87) PCT Pub. No.: WO2007/072069
PCT Pub. Date: Jun. 28, 2007

(65) Prior Publication Data
US 2009/0201032 A1   Aug. 13, 2009

(30) Foreign Application Priority Data

Dec. 19, 2005   (GB) .................................. 0525760.5

(51) Int. Cl.
*G01R 27/08* (2006.01)
(52) U.S. Cl. ...................................................... 324/713
(58) Field of Classification Search .......... 204/400–435; 205/775–794.5
See application file for complete search history.

(56) References Cited

U.S. PATENT DOCUMENTS

| | | | |
|---|---|---|---|
| 4,169,779 A | 10/1979 | Tataria et al. | |
| 4,529,965 A * | 7/1985 | Lee | 341/122 |
| 4,642,172 A | 2/1987 | Fruhwald | |
| 5,214,274 A * | 5/1993 | Yang | 250/208.1 |
| 5,382,331 A * | 1/1995 | Banks | 205/781 |
| 5,583,462 A * | 12/1996 | Grasshoff | 327/262 |
| 6,035,694 A * | 3/2000 | Dupuie et al. | 73/1.38 |
| 6,940,338 B2 * | 9/2005 | Kizaki et al. | 327/543 |
| 2005/0068046 A1* | 3/2005 | Frey et al. | 324/686 |
| 2005/0083110 A1* | 4/2005 | Latham et al. | 327/538 |

FOREIGN PATENT DOCUMENTS

| | | |
|---|---|---|
| EP | 0567725 | 11/1993 |
| WO | WO 2005008286 A2 * | 1/2005 |
| WO | WO 2005074467 A2 * | 8/2005 |

OTHER PUBLICATIONS

Horowitz et al., The Art of Electronics, Second Edition, Cambridge University Press, 1989, pp. 152-153, Fig. 3.54.*

* cited by examiner

*Primary Examiner* — Melissa Koval
*Assistant Examiner* — Daniel Miller
(74) *Attorney, Agent, or Firm* — Patterson & Sheridan, L.L.P.

(57) ABSTRACT

A circuit for operating an amperometric sensor having a reference electrode, a counter electrode and a work electrode. The circuit comprises an amplifier having a positive input and a negative input and an output. The positive input is coupled to a reference voltage source, and the negative input and the output are coupled together via a negative feedback loop. The circuit includes means for coupling the amperometric sensor into said negative feedback loop of the amplifier wherein, in a first configuration, the counter electrode is coupled to said output and the reference electrode is coupled to said negative input and, in a second configuration, the work electrode is coupled to said output and the reference electrode is coupled to said negative input.

17 Claims, 4 Drawing Sheets

SENSOR CIRCUITS

FIELD OF THE INVENTION

The present invention relates to sensor circuits and in particular, though not necessarily, to biasing circuits for amperometric sensors.

BACKGROUND TO THE INVENTION

Amperometric sensors have been used to detect the presence of specific analytes, for example enzymes in liquids, for over 20 years. The basic principle is to effect a reaction between the analyte to be detected in a sample and the sensor surface. The subsequent charge produced is then converted into a sensor current that can be measured. The size of the current is generally related to the quantity of analyte present.

FIG. 1 shows a simplified biasing circuit used in a typical sensor. The circuit consists of three electrodes, a counter electrode C, a work electrode W and a reference electrode R. The counter electrode C and reference electrode R are connected to a work potential setting amplifier, Amp1, and an output buffer amplifier, Amp2, and a current sensing resistor, Rsens as shown in FIG. 1.

The work electrode W is coated with a reaction inducing coating that reacts with the chosen analyte. For example, a glucose sensor might have a glucose oxidase coating on the work electrode W. The reaction produces ions that when subjected to a potential difference give rise to current flow from the counter electrode C to the work electrode W. The current also flows through the current sensing resistor Rsens giving a voltage drop Vout across that resistor. A typical sensor current might be 10 nA, and for Rsens=1 MΩ, Vout is 10n×1M=10 mV referenced to ground. As already noted the size of the current flowing from the counter electrode C to the work electrode W, and hence the output voltage Vout across Rsens, depends on the concentration of the analyte.

The potential on the reference electrode is key to achieving optimum sensor performance. The reaction efficiency at the working electrode W depends on the work potential $V_{RW}$. Different sensors operate best at different values of work potential $V_{RW}$. For example, a glucose sensor operates optimally at $V_{RW}$=0.6V compared to $V_{RW}$=−0.6V for an oxygen sensor. The role of the work potential setting amplifier is to maintain the work potential $V_{RW}$ at the value for which reaction conditions are optimised. This is done by setting the positive terminal of the work potential setting amplifier to Vref=$V_{RW}$+Vout and the negative terminal of the work potential setting amplifier to $V_{RW}$. As mentioned earlier, Vout is the potential drop across the current sensing resistor Rsens due to the sensor current and typically has a value of 10 mV. If the maximum voltage that can be generated across the current sensing resistor by a glucose sensor is, for example, 100 mV, Vref would be set to Vref=0.6V+100 mV to ensure that the reaction conditions are optimised. However, because Vout varies with, for example, analyte concentration and time, the work potential $V_{RW}$ is subject to fluctuations. The fluctuations of the work potential $V_{RW}$ away from Vref are a problem with sensor circuit designs such as that of FIG. 1 as they are detrimental to an efficient reaction at the work electrode W and also impact on the consistency of the output signal.

In practical applications of the sensor, a user may want to measure, for example, both the glucose and oxygen levels using the same sensor system. As already noted, glucose and oxygen sensors operate at different work potentials $V_{RW}$, 0.6V and −0.6V respectively. The sensor system should therefore be able to accommodate both work potentials. If a single circuit of the type shown in FIG. 1 is used, a headroom of more than 1.2V would be required of the circuit voltage supply. However, this would be too large for a single chip low power integrated circuit design running at low voltages of 1V and below.

A possible solution to the voltage limitation problem referred to above is to make a multiple sensor by designing two parallel circuits on a single chip. This is illustrated in FIG. 2. Implementing this solution would require re-referencing the Vref and Vout signals to ground. However, using two parallel circuits increases the used chip area and therefore the costs of producing the chip. In addition to this, the design in FIG. 2 would still not solve the problem caused by fluctuations in the work potential $V_{RW}$.

A further problem which arises with the designs of both FIG. 1 and FIG. 2 is the presence of Shott noise which results from the current sensing resistor. This noise is proportional to the value of the resistance and will be significant relative to the output voltage.

SUMMARY OF THE INVENTION

According to a first aspect of the invention there is provided a circuit for operating an amperometric sensor having a reference electrode, a counter electrode and a work electrode, the circuit comprising:

an amplifier having a positive input and a negative input and an output, the positive input being coupled to a reference voltage source, and the negative input and the output being coupled together via a negative feedback loop; and means for coupling the amperometric sensor into said negative feedback loop of the amplifier wherein, in a first configuration, the counter electrode is coupled to said output and the reference electrode is coupled to said negative input and, in a second configuration, the work electrode is coupled to said output and the reference electrode is coupled to said negative input.

Preferably, the circuit comprises a subtractor having an output coupled to the negative input of the amplifier, wherein, in use:

in said first configuration, a positive input of the subtractor is coupled to the reference electrode and a negative input of the subtractor is coupled to the work electrode; and in said second configuration, the positive input of the subtractor is coupled to the work electrode and the negative input of the subtractor is coupled to the reference electrode.

Preferably, the circuit comprises switching means for switching the circuit between said first and second configurations.

Preferably, said switching means is selectable to toggle the positive and negative inputs of the subtractor.

Preferably, the circuit comprises a capacitance arranged in use to be coupled to one of the work and counter electrodes to integrate sensor current received therefrom, and means for providing the voltage stored on the capacitance to a measurement output.

Preferably, the circuit includes a controller arranged in use to couple said capacitance to one of the counter and work electrodes for a predefined time period, said means for providing the voltage stored on the capacitance to a measurement output operating to provide the voltage at the end of said predefined time period.

Preferably, circuit comprises a discharge switch for selectably coupling the current receiving side of the capacitance to ground in order to discharge any charge stored on the capacitance prior to performing a sensor measurement.

Preferably, said means for providing the voltage stored on the capacitance to a measurement output comprises a unity gain buffer amplifier having a positive input coupled to said current receiving side of the capacitance.

Preferably, said capacitance is a variable capacitance.

Preferably, the circuit comprises one or more constant current sources selectable to provide constant current to said capacitance, and switch means for disconnecting the capacitance from a sensor during charging of the capacitance by a constant current source, wherein measurement of the voltage applied to the capacitance by a constant current allows for circuit and sensor calibration.

Preferably, the circuit comprises a second switching means which, in use, connects at least one sensor electrode to ground to discharge sensor capacitances prior to performing a sensor measurement.

Preferably, the circuit comprises a controller for automatically, or under user instruction, configuring said means for coupling and any switching means.

Preferably, the circuit is integrated into a single semiconductor chip.

Preferably, the circuit comprises a plurality of terminals for coupling to electrodes of an external amperometric sensor.

Preferably, the circuit has a supply voltage of 1V or less.

According to a second aspect of the invention there is provided a sensor system comprising the circuit of the above first aspect of the invention in combination with an amperometric sensor.

According to a third aspect of the invention there is provided a method of operating the sensor system of the above second aspect of the invention comprising:

setting said means for coupling into said first or said second configuration;

integrating current generated by a sensor across a capacitance; and after a predefined time period has elapsed, measuring the voltage stored on the capacitance.

According to a fourth aspect of the invention there is provided a circuit for biasing a sensor and said circuit comprises of an amplifier and a subtractor, the subtractor being coupled into a negative feedback loop of the amplifier and in use having its positive and negative inputs coupled respectively to first and second terminals of the sensor, the output of the amplifier being coupled in use to a sensor terminal, and a positive input of the amplifier being coupled to a reference voltage, wherein the voltage between said first and second terminals is substantially clamped at said reference voltage.

Preferably, the circuit is for use with an amperometric sensor, wherein said first terminal is one of a reference electrode and a work electrode and said second terminal is the other of the reference electrode and the work electrode, and said output of the amplifier is coupled to one of the counter electrode and the work electrode.

Preferably, the circuit is for use with an Ion Sensitive Field Effect Transistor, said first and second terminals being the source and drain of the Ion Sensitive Field Effect Transistor, and said output of the amplifier being coupled to the said source terminal.

According to a fifth aspect of the invention there is provided a circuit for detecting current output from a sensor and comprising a capacitance arranged in use to be coupled to an output of the sensor, means for discharging the voltage across the capacitance prior to a measurement cycle, and means for measuring the voltage stored on the capacitance after a measurement cycle.

DETAILED DESCRIPTION OF CERTAIN EMBODIMENTS OF THE INVENTION

Figure 1:
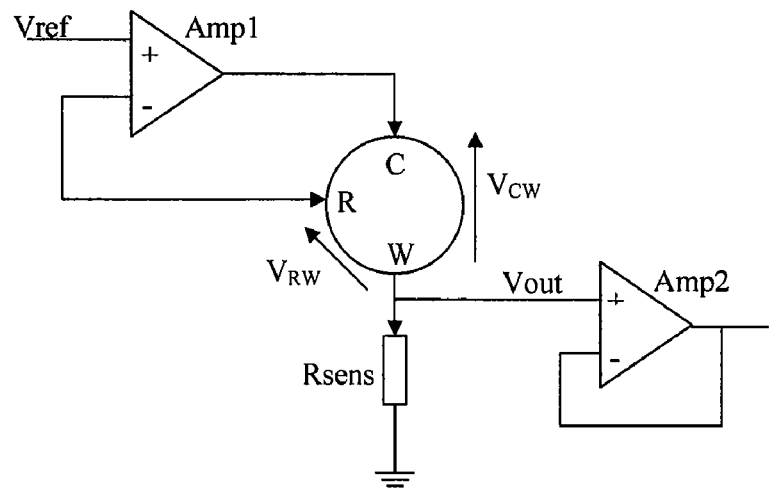
FIG. 1 illustrates schematically a known amperometric sensor biasing and output circuit.
Figure 2:
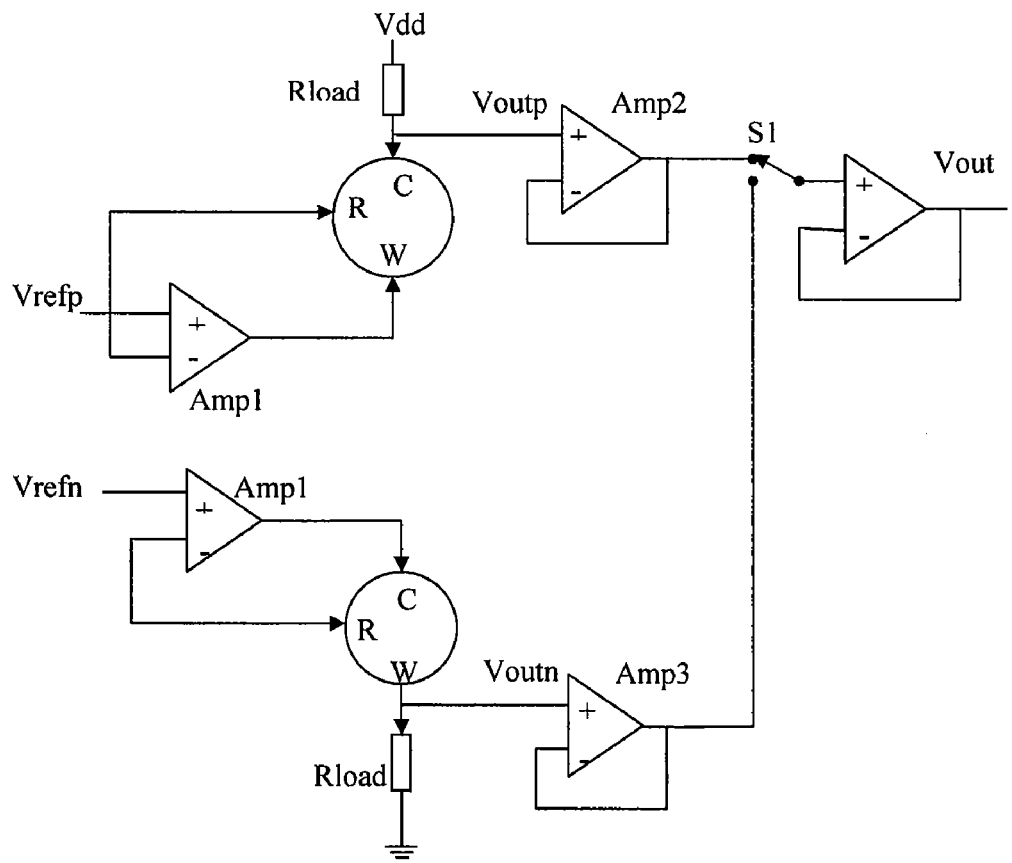
FIG. 2 illustrates schematically a multi-sensor biasing and output circuit.
Figure 3:
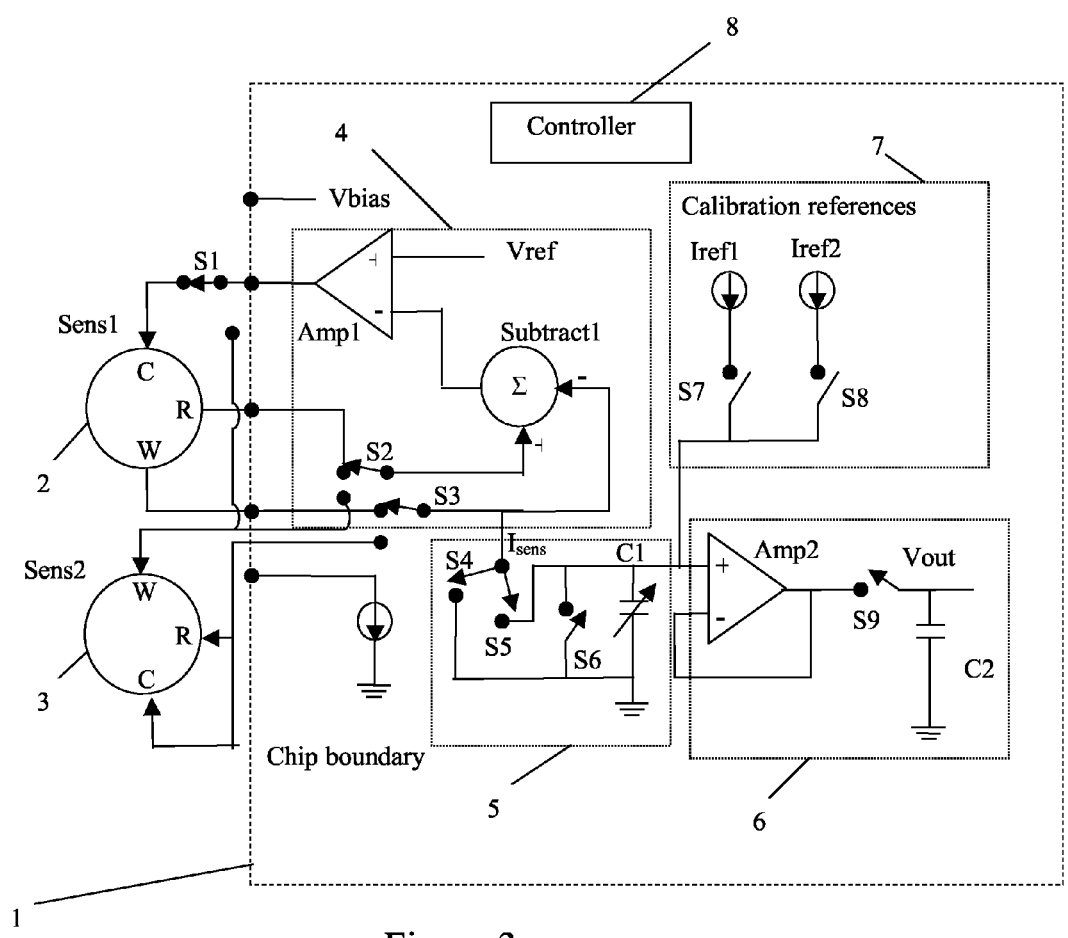
FIG. 3 illustrates schematically a first embodiment of an amperometric sensor biasing and output circuit according to the invention.

The amperometric sensor biasing and output circuit to be described replaces the external current sensing resistor of prior art designs (Rsens of FIGS. 1 and 2) with an on-chip variable capacitor. Such a circuit is illustrated in FIG. 3. It is assumed that the circuit has available to it a supply voltage of only one volt or less.

The circuit is assumed to be integrated into a silicon substrate 1 with two external sensors, Sens1 (reference 2) and Sens2 (reference 3), suitably connected to it; for example sensor Sens1 could be a glucose sensor with an optimal work potential of 0.6V, and sensor Sens2 could be an oxygen sensor with an optimal work potential of −0.6V. However, the sensors 2,3 do not necessarily need to be off-chip and could alternatively be integrated on-chip. Each sensor has a work electrode W, a reference electrode R and a counter electrode C.

A work potential setting circuit 4 comprises a work potential setting amplifier Amp1 and a subtractor Subtract1. The positive terminal of the potential setting amplifier Amp1 is connected to a settable reference voltage Vref. Appropriate positioning of switches S1, S2 and S3 selects one of the two sensors 2,3 as the active sensor. In the case that sensor Sens1 is selected, the switches S1, S2 and S3 are connected as shown in FIG. 3 to configure the circuit as follows:

The potential at the work electrode W is set to an appropriate positive potential with respect to the reference electrode R.

The negative terminal of the amplifier Amp1 is connected to the output terminal of a subtractor Subtract1, whilst the output terminal of the amplifier is connected to the counter electrode C of the sensor Sens1.

The positive terminal of the subtractor Subtract1 is connected to the reference electrode R of the sensor Sens1 via switch S2.

The negative terminal of the subtractor, Subtract1, is connected to the work electrode W of sensor Sens1 via switch S3.

In the case that sensor Sens2 is selected, the switches S1, S2 and S3 are set to positions that are opposite with respect to the positions of the switches S1 to S3 as shown in FIG. 3. In this configuration, the output terminal of the work potential setting amplifier Amp1 is connected to the work potential electrode W of sensor Sens2 and the negative terminal of the work potential setting amplifier is connected to the output terminal of the subtractor Subtract1. The negative terminal of the subtractor Subtract1 is connected to the reference electrode R of sensor Sens2, and the positive terminal of the subtractor Subtract1 is connected to the work electrode W of sensor Sens2.

Reference numeral 5 identifies a current detection circuit comprising switches S4, S5 and S6 and a variable capacitor C1 connected at one side to ground. Reference numeral 6 identifies an output circuit comprising a buffer amplifier Amp2, a capacitor C2 connected at one side to ground, and a capacitor discharge switch S9. Reference numeral 7 identifies a calibration circuit comprising reference current sources, Iref1 and Iref2, that are used to calibrate the sensor system as will be described below.

A controller 8 controls the setting of switches S1 to S9, circuit timings, the value of the variable capacitor C1, the value of Vref and the current sources Iref1 and Iref2 according to user inputs and/or pre-programmed instructions.

Figure 4:
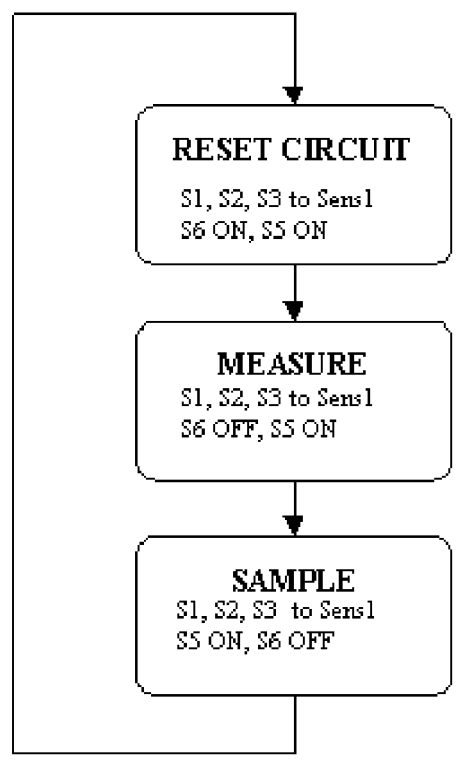
FIG. 4 is a flow chart illustrating the steps involved in measuring the current from an amperometric sensor using the circuit of FIG. 3.
Figure 5:
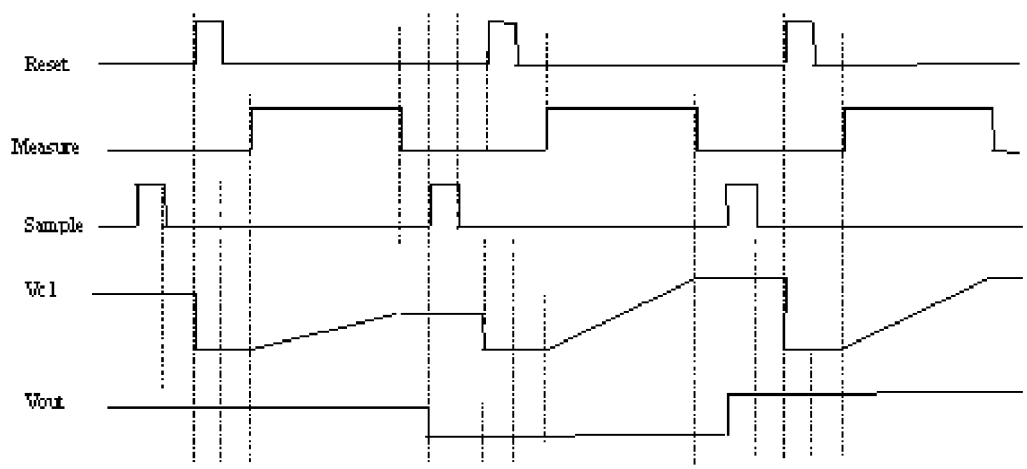
FIG. 5 is a signalling diagram showing the voltages across the circuit of FIG. 3 for measurement cycles corresponding to three different sensor currents.

Let us consider how the circuit measures the sensor current Isens for a chosen sensor. This is illustrated in the flow chart of FIG. 4. The voltages at a number of points within the circuit are shown in FIG. 5 for three different measurement cycles. Upon user activation to obtain a measurement, the controller 8 initiates the measurement process by fully discharging the capacitors C1, C2 and any sensor capacitances. This is done by opening switch S4 and closing switches S5, S6 and S9. In the case that sensor Sens1 is selected, the controller 8 then sets switches S1, S2 and S3 to the positions shown in FIG. 3 to ensure an appropriate positive voltage on the work electrode of sensor Sens1 with respect to the reference electrode R. The controller 8 initiates a timer.

As will be clear from FIG. 3, the subtractor Subtract1 provides to the negative terminal of the work potential setting amplifier Amp1, a voltage equal to the work potential $V_{RW}$. The work potential setting amplifier Amp1 seeks, via the negative feedback loop, to drive its negative terminal voltage to the positive input voltage Vref. The voltage $V_{RW}$ is thus clamped at the reference voltage Vref chosen by the controller 8, ensuring that the reaction conditions are optimised.

The analyte, for example glucose, reacts at the work electrode W and produces an ionic charge. This charge modulates the conductivity of the path between the work and counter electrodes, resulting in a current Isens flowing between the electrodes. The sensor current Isens flows from the work electrode W via switches S3 and S5 to the capacitor C1, creating a potential difference across the capacitor C1. After the timer has reached some predefined value T1, the controller 8 opens switch S5. The voltage held on the capacitor C1 is Vsens=Isens×(T1/C1).

The controller 8 starts a second timer. The voltage Vsens is applied to the positive terminal of the buffering amplifier Amp2. The negative feedback loop on the amplifier Amp2 causes the output voltage on the amplifier to equal the voltage Vsens. The capacitors C1 and C2 are then reset as above in readiness for a further measurement cycle.

The switch S9 can be used to isolate the voltage on the capacitor C2 to make the voltage available for processing while sensor current is integrated on the capacitor C1 to perform a new measurement. In this case, the switch S9 is opened prior to the sensor Sens1 and capacitor C1 being discharged, before the start of a second measurement cycle. The voltage is thus isolated on the capacitor C2. The capacitor C2 is discharged only just prior to switch S9 being closed to latch a further output voltage.

If the user (or controller) chooses to measure an analyte that requires a negative work potential $V_{RW}$, the controller 8 selects sensor Sens2 as the active sensor. The work electrode W is driven to the reference voltage Vref by the same driving mechanism described earlier. However, the work potential $V_{RW}$ will be −Vref because of the difference in the way the sensor Sens2 is connected to the subtractor compared to Sens1. Again, during the measurement phase, the sensor current Isens flows via switches S3 and S5 onto the capacitor C1, creating a potential difference across it, and after time T1 has elapsed the output voltage can be generated by the output circuit 6.

The circuit of FIG. 3 includes a number of features which ensure that the operation is configurable to handle a wide variety of sensor types and sensor sensitivities, and to compensate for errors such as those introduced by manufacturing tolerances. For example, the controller 8 can dynamically adjust the charging time T1 of the sensing capacitor C1, or the value of the variable capacitor C1 (which may be provided by a bank of switchable capacitances). In addition, the controller 8 can be arranged to perform a calibration by measuring the sensor current when the sensor is off (i.e. is not immersed in the analyte solution) to allow leakage currents to be measured and therefore compensated for in the sensor measurements when the sensor is turned on.

During a calibration cycle controlled by the controller 8, the current measurement circuit can be referenced to standard on-chip constant currents, allowing for the effects of manufacturing tolerances, offsets and drifts to be compensated for. This is done by selectively connecting the reference current sources Iref1 and Iref2 to the measurement circuit via switches S7 and S8, with switches S5 and S6 open. The controller 8 closes switch S4 to discharge any charge on the sensor, discharges the voltage across the sensing capacitor C1, and then selects one or both of the reference current sources as appropriate for the values set for the sensing capacitor C1 and charging time T1. If for example only Iref1 is applied, the voltage resulting at the output is Vref1=Iref1×(T1/C1). In a subsequent measurement cycle, a voltage Vsens=Isens×(T1/C1) is obtained at the output. The ratio of the two voltages, Vref1/Vsens=Iref1/Isens is independent of the capacitor value.

The circuit of FIG. 3 provides a number of significant advantages over prior art sensor circuit designs. In particular, the circuit eliminates Shott noise due to the sensing resistance of prior art designs. Noise resulting from the sensing capacitor C1 is significantly less than the eliminated Shott noise. Elimination of the sensing resistance also reduces chip area. Due to the improved voltage clamping of the work potential, the reaction rate is maintained at an optimum value and will not fluctuate as a result of voltage drop across the current sensing circuit.

Figure 6:
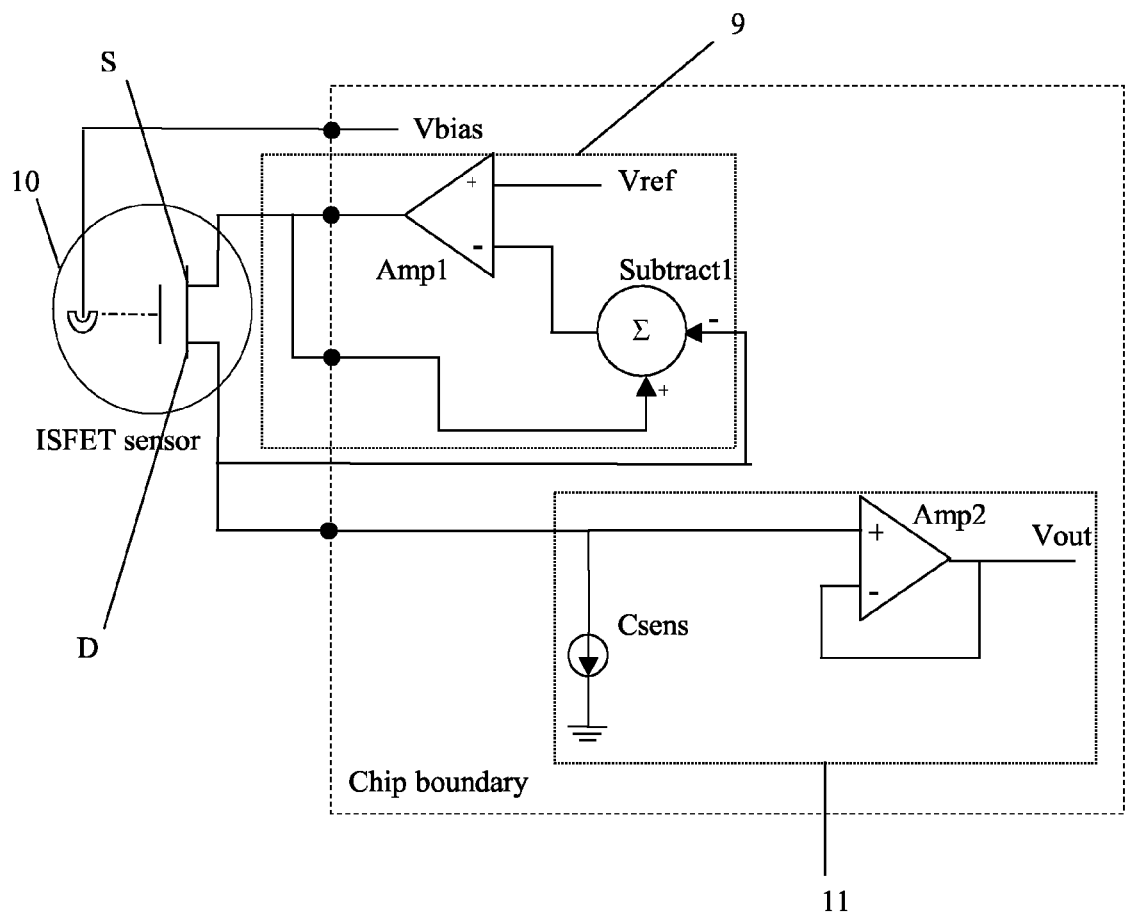
FIG. 6 illustrates schematically a biasing and output circuit for an Ion Sensitive Field Effect Transistor.

Considering now a further aspect of the invention, it will be appreciated that the work potential setting circuit 4 of FIG. 3 can also be used as a potential setting circuit in an Ion Sensitive Field Effect Transistor (ISFET) sensor circuit. This is illustrated in FIG. 6, where the potential setting circuit is indicated by reference numeral 9, the ISFET sensor by reference numeral 10, and an output circuit by reference numeral 11. The ISFET source terminal is connected to the output of the potential setting amplifier Amp1. The ISFET drain terminal is connected to the negative terminal of the subtractor Subtract1 and the positive terminal of the subtractor Subtract1 is connected to the output terminal of the potential setting amplifier Amp1. The positive terminal of the potential setting amplifier is at a reference voltage Vref.

The potential setting circuit 1 works according to the same principles as described with reference to FIG. 3, i.e. the source-drain voltage $V_{SD}$ is clamped at Vref. With a bias voltage Vbias applied to the solution containing the analyte, the reaction at the gate electrode modulates the amount of charge in the channel beneath the gate of the ISFET and hence the source-drain current which flows through a current sensor Csens, which might, for example, be a resistor or the current detection circuit 5 of FIG. 3.

It will be appreciated by the person of skill in the art that various modifications may be made to the above described embodiment without departing from the present scope of the invention.

The invention claimed is:

1. A circuit for operating a first amperometric sensor and a second amperometric sensor, each having a reference electrode, a counter electrode and a work electrode, wherein the first amperometric sensor is configured to operate at a positive work potential and the second amperometric sensor is configured to operate at a negative work potential, the circuit comprising:

an amplifier having a positive input and a negative input and an output, the positive input being coupled to a single reference voltage source for outputting a settable single positive reference voltage, and the negative input and the output being coupled together via a negative feedback loop;

a subtractor within said negative feedback loop and having an output coupled to the negative input of the amplifier;

switching means which when set in a first configuration causes the single reference voltage source to positively bias the first amperometric sensor with a positive work potential by coupling the first amperometric sensor into said negative feedback loop of the amplifier such that the counter electrode of the first sensor is coupled to said output, a positive input of the subtractor is coupled to the reference electrode of the first sensor, and a negative input of the subtractor is coupled to the work electrode of the first sensor, and which when set in a second configuration causes the single reference voltage source to negatively bias the second amperometric sensor with a negative work potential by coupling the second amperometric sensor into said negative feedback loop such that the work electrode of the second sensor is coupled to said output, the positive input of the subtractor is coupled to the work electrode of the second sensor, and the negative input of the subtractor is coupled to the reference electrode of the second sensor.

2. A circuit according to claim 1, and comprising a capacitance coupled to the work electrodes to integrate sensor current received therefrom, and means for providing the voltage stored on the capacitance to a measurement output.

3. A circuit according to claim 2 and comprising a controller arranged in use to couple said capacitance to the work electrodes for a predefined time period, said means for providing the voltage stored on the capacitance to a measurement output operating to provide the voltage at the end of said predefined time period.

4. A circuit according to claim 2 and comprising a discharge switch for selectably coupling the current receiving side of the capacitance to ground in order to discharge any charge stored on the capacitance prior to performing a sensor measurement.

5. A circuit according to claim 2, wherein said means for providing the voltage stored on the capacitance to a measurement output comprises a unity gain buffer amplifier having a positive input coupled to said current receiving side of the capacitance.

6. A circuit according to claim 2, wherein said capacitance is a variable capacitance.

7. A circuit according to claim 2 and comprising one or more constant current sources selectable to provide respective constant currents to said capacitance, and switch means for disconnecting the capacitance from a sensor during charging of the capacitance by a constant current source, wherein measurement of the voltage applied to the capacitance by a constant current allows for circuit and sensor calibration.

8. A circuit according to claim 1 and comprising second switching means which, in use, is settable to connect at least one sensor electrode to ground to discharge sensor capacitances prior to performing a sensor measurement.

9. A circuit according to claim 1 and comprising a controller for automatically setting said switching means into said first or said second configuration.

10. A circuit according to claim 1, the circuit being integrated into a single semiconductor chip.

11. A circuit according to claim 10 and comprising a plurality of terminals for coupling to electrodes of an external amperometric sensor.

12. A circuit according to claim 1 where a supply voltage is 1V or less.

13. A sensor system comprising a circuit according to claim 1 in combination with an amperometric sensor.

14. A sensor system according to claim 13 which further comprises a capacitance coupled to the work electrode to integrate sensor current received therefrom, and means for providing the voltage stored on the capacitance to a measurement output.

15. A circuit according to claim 1, further comprising a controller for setting a value of the positive reference voltage output by the reference voltage source.

16. A method of operating a sensor system comprising a first amperometric sensor and a second amperometric sensor, wherein each amperometric sensor has a reference electrode, a counter electrode, and a work electrode and, in operation, the first amperometric sensor is configured to operate at a positive work potential and the second amperometric sensor is configured to operate at a negative work potential, the method comprising:

setting a switching means to one of first and second configurations, wherein:

when set in the first configuration the switching means causes a single reference voltage source to positively bias the first amperometric sensor with a positive work potential by coupling the first amperometric sensor into a negative feedback loop of an amplifier in the first configuration, when set in the second configuration the switching means causes the single reference voltage source to negatively bias the second amperometric sensor with a negative work potential by coupling the second amperometric sensor into the negative feedback loop in the second configuration, the amplifier has a positive input and a negative input and an output, the positive input is coupled to the single reference voltage source, wherein the single reference voltage source outputs a settable single positive reference voltage, the negative input and the output are coupled together via the negative feedback loop, the negative feedback loop has a subtractor having an output coupled to the negative input of the amplifier, the first counter electrode is coupled to the output in the first configuration, a positive input of the subtractor is coupled to the first reference electrode in the first configuration, a negative input of the subtractor is coupled to the first work electrode in the first configuration, the second work electrode is coupled to the output in the second configuration, the positive input of the subtractor is coupled to the second work electrode in the second configuration, and the negative input of the subtractor is coupled to the second reference electrode in the second configuration;

integrating current generated by the set sensor across a capacitance coupled to the set work electrode; and after a predefined time period has elapsed, measuring a voltage stored on the capacitance.

17. A method according to claim 16, further comprising setting a value of the positive reference voltage output by the reference voltage source.

* * * * *